United States Patent
Noller

Patent Number: 6,083,157
Date of Patent: Jul. 4, 2000

[54] METHOD AND APPARATUS FOR THE NON-INVASIVE DETERMINATION OF THE CONCENTRATION OF A COMPONENT

[75] Inventor: Friedemann Noller, Herrenberg, Germany

[73] Assignee: Hewlett-Packard Company, Palo Alto, Calif.

[21] Appl. No.: 09/040,354

[22] Filed: Mar. 10, 1998

[30] Foreign Application Priority Data

Apr. 12, 1997 [EP] European Pat. Off. .............. 97106032

[51] Int. Cl.$^7$ .................................................... A61B 5/00
[52] U.S. Cl. ........................... 600/310; 600/336; 600/479
[58] Field of Search .................................. 600/310, 322, 600/323, 324, 330, 336, 479, 481, 483, 504

[56] References Cited

U.S. PATENT DOCUMENTS

| | | |
|---|---|---|
| 4,824,242 | 4/1989 | Frick et al. . |
| 5,216,598 | 6/1993 | Branstetter et al. . |
| 5,285,782 | 2/1994 | Prosser ..................................... 600/324 |

FOREIGN PATENT DOCUMENTS

| | | |
|---|---|---|
| 262778A1 | 8/1987 | European Pat. Off. . |
| 265952A2 | 10/1987 | European Pat. Off. . |
| 504725A2 | 3/1992 | European Pat. Off. . |

Primary Examiner—Eric F. Winakur

[57] ABSTRACT

A method of determining the concentration of a component from the intensity of electromagnetic waves with at least two selected wavelengths which are reflected by human tissue or transmitted through human tissue comprises the step of converting first intensities of the received electromagnetic waves into at least one first and one second electric signal. Following this, a continuous first temporal average value of the first signal and a continuous second temporal average value of the second signal are formed. A first alternating component is continuously determined from said first signal and said first average value, whereas a second alternating component is continuously determined from said second signal and said second average value. Subsequently, a continuous ratio is determined from said first and second signals as well as from said first and second continuous temporal average values, with the exception of regions lying close to the zero passages of the alternating components. Finally, the concentration of the component is derived from said continuous ratio or from the integrated ratio derived from the integrated alternating components.

18 Claims, 5 Drawing Sheets

METHOD AND APPARATUS FOR THE NON-INVASIVE DETERMINATION OF THE CONCENTRATION OF A COMPONENT

DESCRIPTION

The present invention refers to methods and apparatus for the non-invasive determination of the concentration of a component, e.g. for determining the oxygen saturation of arterial blood, on the basis of the intensity of electromagnetic waves with at least two selected wavelengths which are reflected by human tissue or transmitted through human tissue.

The methods and apparatuses according to the present invention can, for example, be used in an advantageous manner for measuring and calculating the oxygen saturation.

Oxygen saturation is a clinically very relevant parameter to assess the condition of a patient. Particularly in the operating room, the oxygen saturation of the blood gives an indication of the patient's condition, its supply with oxygen and other physiological factors.

One possibility to obtain a very precise value of the patient's oxygen saturation is to take a blood sample and analyze it in a blood gas analyzer. Despite the high precision of this method, it is an invasive technique and this means that it cannot performed frequently, i.e. does not allow continuous monitoring. Therefore, significant changes in the oxygen saturation value may be missed. Last not least, it is understood that an invasive technique is not the preferred way to monitor a patient.

It is therefore highly desirable to measure oxygen saturation non-invasively. This can be achieved by a technique called pulse oximetry.

An pulse oximeter usually comprises two or more light sources of different wave length. The light is irradiated on human flesh, and either the intensity of the light transmitted through the flesh, or the intensity of the reflected light is measured. In more general terms, "light" does not only mean electromagnetic waves in the visible spectrum. For example, the most common oximeters use one wavelength in the visible spectrum and another wavelength in the infrared spectrum. Such a pulse oximeter is described for example in "A New Family of Sensors for Pulse Oximetry", S. Kästle, F. Noller et al, February 1997, Hewlett-Packard Journal.

For more details on the theory of oxygen saturation measurement, reference is made to former publications on this subject, e.g. U.S. Pat. No. 4,167,331 or EP-A-262778 (the latter patent application contains a quite complete breakdown of the theory).

The intensities received in pulse oximetry methods show time-dependent superpositions. Furthermore, the known methods calculate the oxygen saturation with regard to the peak values of the intensities received. In addition, said known methods are not able to carry out an exact saturation calculation when the intensities received are superimposed by so-called "motion artifacts" caused e.g. by a displacement of the LEDs and of the photodiodes, which are used for transmitting and for receiving electromagnetic waves, relative to e.g. a finger as test specimen. Known methods of determining the arterial oxygen saturation are therefore inaccurate due to time-dependent superpositions of the intensities received, and they are susceptible to components in the alternating signal time spectrum which have the same or higher frequencies: known determination methods do not provide useful results in this case.

Hence, it is the object of the present invention to provide methods and apparatus for a precise and insusceptible determination of the concentration of a component, e.g. the arterial oxygen saturation, on the basis of the intensity of electromagnetic waves with at least two selected wavelengths which are reflected by human tissue or transmitted through human tissue.

This object is achieved by methods according to claims 1 and 7 as well as by apparatuses according to claims 13 and 14.

It is also an object of the present invention to provide a method and an apparatus for determining a pulse rate of a flow of blood through human tissue on the basis of the intensity of electromagnetic waves with at least two wavelengths which are reflected by human tissue or transmitted through human tissue.

This object is achieved by a method according to claim 12 and an apparatus according to claim 16.

In accordance with a first aspect, the present invention provides a method of determining the concentration of a component from the intensity of electromagnetic waves with at least two selected wavelengths which are reflected by human tissue or transmitted through human tissue, said method comprising the following steps:

converting the intensities of the received electromagnetic waves into at least one first and one second electric signal;

forming a continuous first temporal average value of the first signal;

forming a continuous second temporal average value of the second signal;

continuously determining a first alternating component from said first signal and said first average value;

continuously determining a second alternating component from said second signal and said second average value;

determining a continuous ratio from said first and second signals as well as from said first and second continuous temporal average values with the exception of regions lying close to the zero passages of the alternating components; and deriving the concentration of the component from said continuous ratio.

The continuous ratio and SpO2 values derived in accordance with the method of the present invention are stable for a period which is longer than a full pulse period and their scattering is low, even if the diastolic region is reached. The method according to the present invention also permits a determination of the pulse rate of perfusion on the basis of the zero passages of the first and second alternating components determined. In contrast to known methods where gaps in the pulse-rate and SpO2 determination frequently occur when perfusion is low and when an additional disturbance occurs, the method according to the present invention permits a continuous derivation of continuous values having a small scattering width and therefore a small standard deviation or of values averaged over one pulse length and having a small scattering width.

In accordance with a further aspect, the present invention provides a method of determining the concentration of a component from the intensity of electromagnetic waves with at least two selected wavelengths which are reflected by human tissue or transmitted through human tissue, said method comprising the following steps:

converting the intensities of the received electromagnetic waves into at least one first and one second electric signal;

forming a continuous first temporal average value of the first signal;

forming a continuous second temporal average value of the second signal;

continuously determining a first alternating component from said first signal and said first average value;

continuously determining a second alternating component from said second signal and said second average value;

determining a continuous differential value of the two alternating components;

determining a first integrated average value by integrating the first average value over a subperiod of said continuous differential value;

determining a second integrated average value by integrating the second average value over said subperiod;

determining an integrated alternating component by integrating the first or the second alternating component over said subperiod;

determining a first integrated value by integrating said differential value over said subperiod;

judging the instantaneous first or second alternating component as disturbance free or as subjected to a disturbance;

if the instantaneous first or second alternating component is judged as disturbance free:

determining an integrated ratio value an the basis of the integrated differential value, the integrated alternating component and the two integrated average values; and deriving the concentration of the component from the integrated ratio value; and otherwise:

determining an integrated ratio value on the basis of the integrated differential value, on the basis of the integrated alternating component determined during the preceding subperiod for which the integrated alternating component determined has been judged as disturbance free, and on the basis of the two integrated average values whose ratio rests constant under artifacts, but not at sudden Sp02 changes; and deriving the concentration of the component from the integrated ratio value.

It follows that the oxygen saturation can be determined by means of the method in accordance with this aspect of the present invention even if the alternating signal spectrum of the intensities received contains disturbance components having the same or higher frequencies.

In accordance with a further aspect, the present invention provides a method of determining a pulse rate of a flow of blood through human tissue from the intensity of electromagnetic waves with at least two selected wavelengths which are reflected by said human tissue or transmitted through said human tissue, said method comprising the following steps:

converting the intensities of the received electromagnetic waves into at least one first and one second electric signal;

forming a continuous first temporal average value of the first signal;

forming a continuous second temporal average value of the second signal;

continuously determining a first alternating component from said first signal and said first average value;

continuously determining a second alternating component from said second signal and said second average value;

determining a continuous differential value of the two alternating components; and determining the pulse rate of the flow of blood on the basis of the zero passages of said differential value.

The present invention also provides apparatus for carrying out the respective methods.

In the following, preferred embodiments of the present invention will be described in detail with reference to the drawings enclosed, in which.

An apparatus which is adapted to be used for carrying out the method according to the present invention comprises at least two transmitting means, preferably light-emitting diodes (LEDs), and at least one photoelectric receiver, e.g. a phototransistor or a photodiode. The LEDs emit light with different wavelengths into the human tissue, e.g. a human finger or a human ear. One of the LEDs can, for example, emit light with a wavelength of 650 nm (red), whereas the other LED can emit light with a wavelength of 940 nm (infrared). Light that has been emitted by these LEDs is transmitted into and reflected by the human tissue, the intensity of the transmitted or reflected light being received by means of the photoelectric receiver, which can also be a receiver responding to both wavelengths. Signals produced by the photoelectric receiver or the photoelectric receivers are fed into e.g. a current-to-voltage converter and, subsequently, they are supplied to an analog-to-digital converter so as to produce digital values on the basis of said signals. The digital values are supplied to a processing unit which carries out the methods of detecting the concentration of the component, e.g. the arterial oxygen saturation, according to the present invention. The processing unit can be a microprocessor of the type normally used in the field of technology, which is provided with a memory, input and output devices (e.g. keyboard, screen and printer) as well as interfaces leading to further processing systems.

Making reference to FIG. 1 to 3, a preferred embodiment of the method according to the first aspect of the present invention will first be explained hereinbelow. This method permits the derivation of the maximum Sp02 information from the raw-wave data so that a reliable Sp02 value, including the pulse rate and the perfusion, can be guaranteed also under low perfusion conditions.

In order to obtain an arterial alternating component value (AC value) which is as "pure" as possible, all the other time-dependent superpositions must, as far as possible, be separated from said alternating component value. For this purpose, the method according to the present invention includes the step of forming continuous average values L1avg[i], L2avg[i] on the basis of raw waves L1[i] and L2[i], L1[i] referring e.g. to the red signal and L2[i] to the infrared signal. These continuous average values can be referred to as baseline. The baseline for the red signal is determined e.g. by means of the following equation:

$$\text{baseline(red)}[i] = L1avg[i] = 1/T \sum_{n=i-T/2}^{i+T/2} L1[n] \quad (1)$$

wherein T is the number of samples per pulse period. When the pulse rate (PR) is 75 beats per minute (bpm), the resultant pulse period is 800 ms; when T is preset to 100, a sample will, consequently, be detected every 8 ms. A baseline for the infrared signal is determined in the same way.

Figure 1:
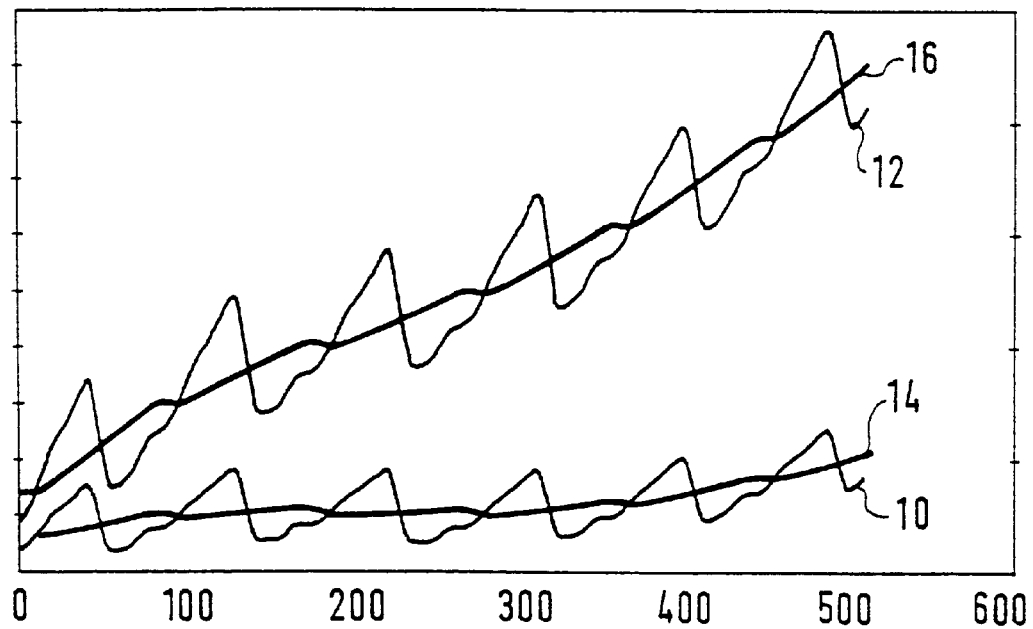
FIG. 1 shows a diagram of recorded first and second signals as well as of the associated continuous average values.
Figure 2:
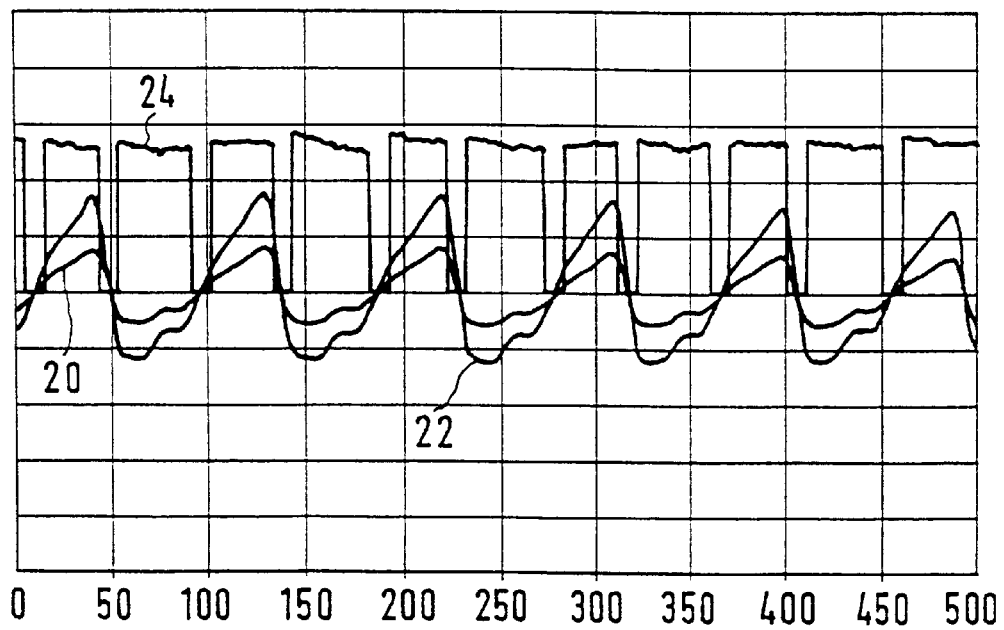
FIG. 2 shows a diagram of the continuous ratio determined, with excluded zero points.

In FIG. 1, the raw waves L1[i] are shown as curve 10, L2[i] as curve 12, and the determined baselines L1avg[i] as curve 14 and L2avg[i] as curve 16, for the red signal and the infrared signal. It can be seen that the constant component dynamics are also effective between the systole and the diastole.

Figure 4:
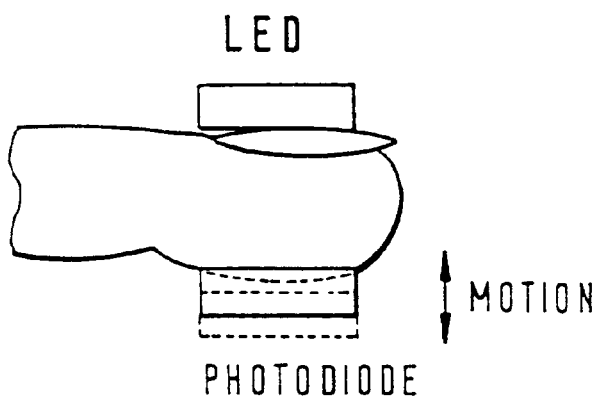
FIG. 4 shows a schematic representation of a test specimen with transmitting LEDs and receiving photodiodes.

At this point, reference should be made to the fact that the ordinate defines the number of samples, whereas the abscissa defines the number of normalized amplitudes in each of the diagrams shown in the figures, with the exception of FIG. 4.

In the method according to the present invention, an AC separation for determining the alternating components is now carried out with the aid of the baseline by means of difference formation. For the red signal, the alternating component AC1[i] is obtained according to the following equation:

$$AC1[i]=L1[i]-L1avg[i] \quad (2)$$

The alternating component AC2[i] for the infrared signal is determined in an analogous manner. It follows that, in addition to the AC information, there are two pulse waves in which the baseline drift is continuously compensated for by the above difference formation.

On the basis of the alternating components which are obtained from the raw waves and from the baselines, a continuous ratio R[i] can directly be derived according to the following equation:

$$R[i]=\ln(L1[i]/L1avg[i])/\ln(L2[i]/L2avg[i]) \quad (3)$$

In this connection, it is, however, of decisive importance that none of the cases with a 0/0 condition nor their neighbourhood is used for calculating the ratio, i.e. all zero passages of the alternating components AC1 and AC2 and their neighbourhoods are excluded from the calculation. Ten samples before a zero passage and after a zero passage can, for example, be excluded from the calculation. The alternating components AC1, curve 20, AC2, curve 22, and the continuous ratio R[i] with excluded zero points, curve 24, are shown in FIG. 2. A normalized average value of 1.07 with a standard deviation of +0.03 is here obtained for the ratio over an interval of 512 samples.

By excluding the zero passages and their neighbourhood, the values are quasi prefiltered or rather reduced to values containing genuine arterial information. The ratio values obtained can be used for determining the respective continuous SpO2[i] values. The individual SpO2[i] values can be obtained in the manner known in accordance with the converter codings, for example.

Figure 3:
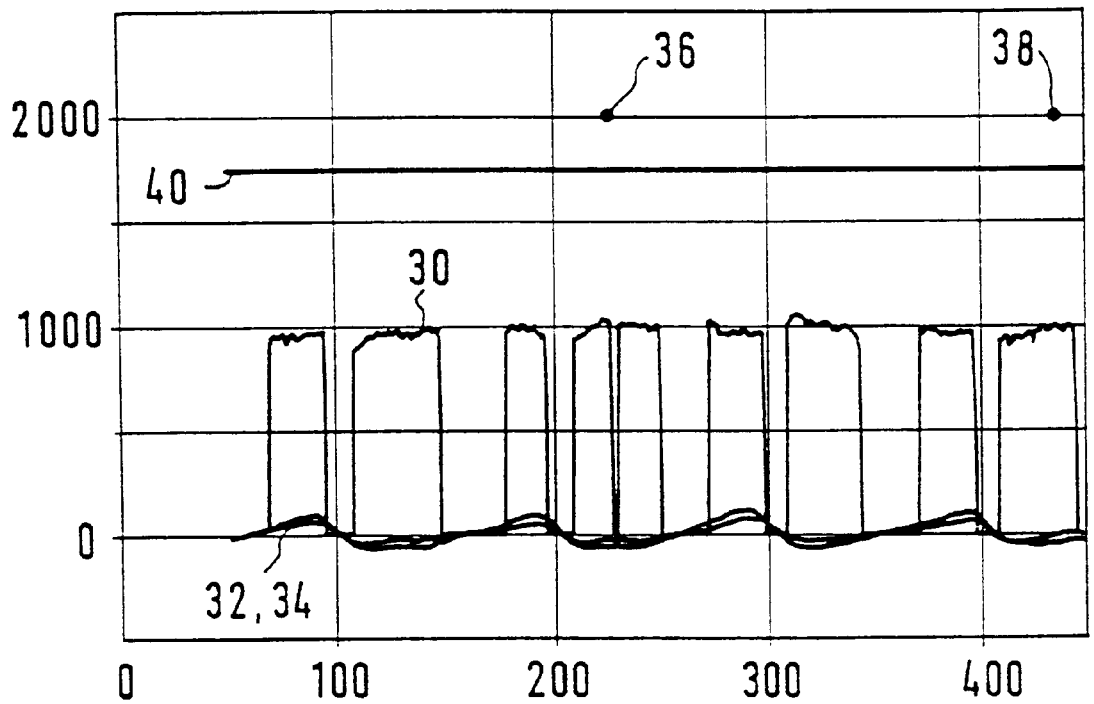
FIG. 3 shows a diagram for elucidating the result of the method according to the present invention in comparison with a known method.

SpO2 values obtained in one example are shown in FIG. 3 as curve 30. These SpO2 values were obtained in a low perfusion episode by means of an ear sensor; with the exception of zero points and their neighbourhood, the SpO2 values were derived continuously. FIG. 3 also shows the alternating components of the red signal and of the infrared signal as curves 32, 34. The ordinate of the diagram shown in FIG. 3 is scaled relative to 100%=1,000. The abscissa represents the number of samples i. Unfiltered beat-to-beat SpO2 values, which were obtained by means of a known algorithm, viz. the "CMS-SpO2 Algorithmus", are additionally shown in said diagram as markers 36 and 38 on a scale that is twice as large as that of the SpO2 values obtained in a accordance with the method according to the present invention and shown in said diagram.

In the example shown, the average value of the SpO2 value determined over 512 samples is 96.7%, the standard deviation being ±3.0%. For comparative reasons, the average value over 5,120 samples (an episode duration of approx. 40 seconds) was calculated. This average value is 97.3%, the standard deviation being ±0.6%.

In comparison with the known algorithm, the method according to the present invention shows a clear improvement with regard to the standard deviation, especially when the average value is calculated over 5,120 samples.

Furthermore, the continuous ratio and SpO2 values derived in accordance with the present invention are stable for a period which is longer than a full pulse period and their scattering is low, even if the diastolic region is reached.

In view of the fact that, in the above-mentioned method according to the present invention, the average value instead of the maximum value (diastole) is taken into account upon calculating the ratio, a small correction factor which depends on the perfusion results in comparison with the classical calculation:

$$Rk=\ln(L1\min/L1\max)/\ln(L2\min/L2\max) \quad (4)$$

namely $$Rcor=R\cdot(2-AC2/L2)/(2-AC1/L1) \quad (5)$$

wherein L1min, L1max, L2min, L2max stand for the minimum and for the maximum values of the red wave and of the infrared wave, respectively. The correction factor, however, does not become significant in the SpO2 until perfusions reach a value of >10%, and in these cases it can be corrected.

In the case of low perfusion and an additional disturbance, respective beat and, consequently, SpO2 gaps frequently occur when the above-mentioned CMS algorithm is used, whereas, by means of the method described hereinbefore, values can continuously be derived in the form of continuous values or in the form of values averaged over one pulse length; in comparison with the known algorithm, said values have half the scattering width. The continuous alternating component curves ascertained can additionally be used for deriving therefrom the pulse rate; this is preferably done by detecting the respective zero passage, i.e. a sign reversal. This will reduce a possible faulty triggering, which takes place frequently at intermediate maxima ("Dichrotie") and due to the influence of artifacts when the classical "peak-finding" method is used.

An interesting parameter is also obtained, when the continuous DC ratio is formed according to the following formula:

$$DC\_Ratio[i]=L1avg[i]/L2avg[i] \quad (6)$$

This ratio remains very stable, even if motion artifacts occur, as long as the sensor does not change its position. In shorter low-perfusion or artifact phases, a monitoring SpO2- or hold-function can be incorporated in this way for bridging said phases. For the above example, this DC ratio is shown in FIG. 3 as curve 40 with averaging over 5,120 samples. A sudden drop or change of arterial SpO2 will also change this value.

In the following, an embodiment of a method according to the second aspect of the present invention will be described on the basis of FIG. 4 to 10.

By means of the above-described continuous baseline method, all low-frequency disturbance components (fs_low<pulse and averaging rate 1/Tp and 1/T, respectively) have been eliminated. Hence, the only components which are still effective as a disturbance in the AC spectrum are components having the same or higher frequencies. A motion artifact caused mainly by a displacement of the LEDs or of the photodiodes relative to the finger or the arterial volume is such an interference. A schematic representation illustrating such a motion is shown in FIG. 4.

When such an artifact occurs, the same deflection a[i] results for both AC signals AC1[i] and AC2[i]. In a first approximation the respective disturbance-modulated signals ACs[i] are therefore given by $$AC1s[i]=AC1[i]+a[i] \quad (7)$$

$$AC2s[i]=AC2[i]+a[i] \quad (8)$$

Figure 5:
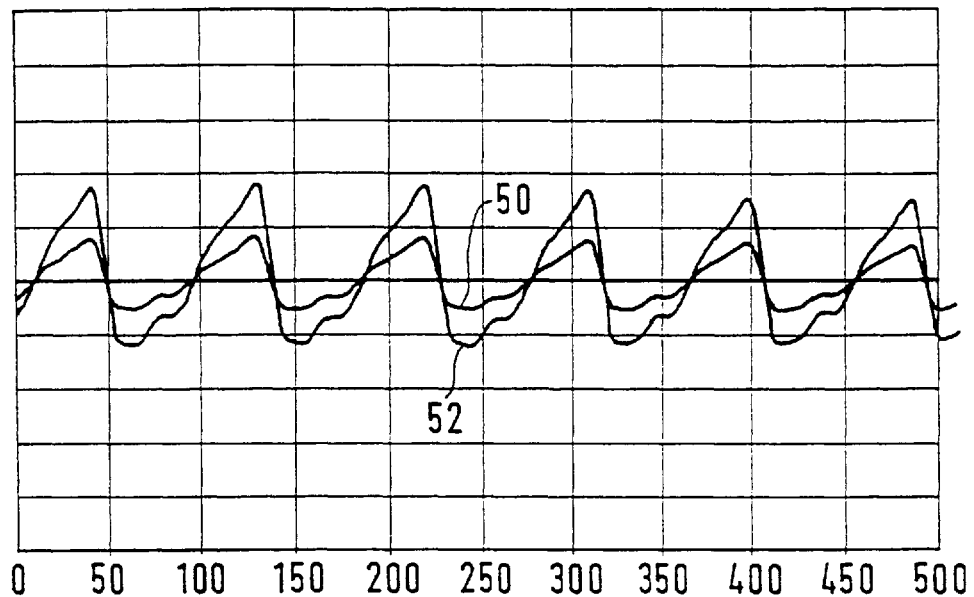
FIG. 5 shows a diagram of two typical undisturbed alternating components.
Figure 6:
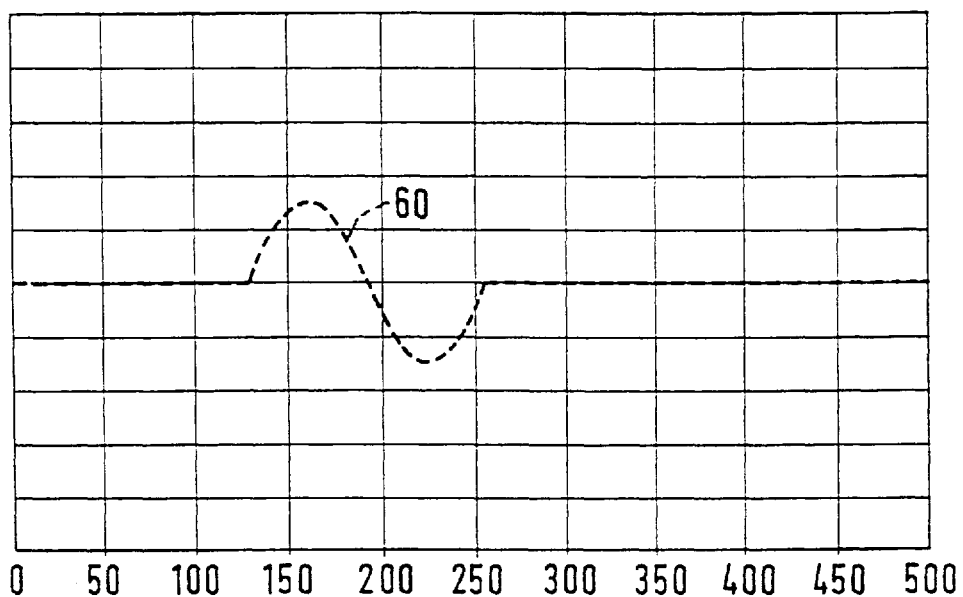
FIG. 6 shows a schematic representation of an intensity change having a higher frequency and caused by a motion artifact.
Figure 7:
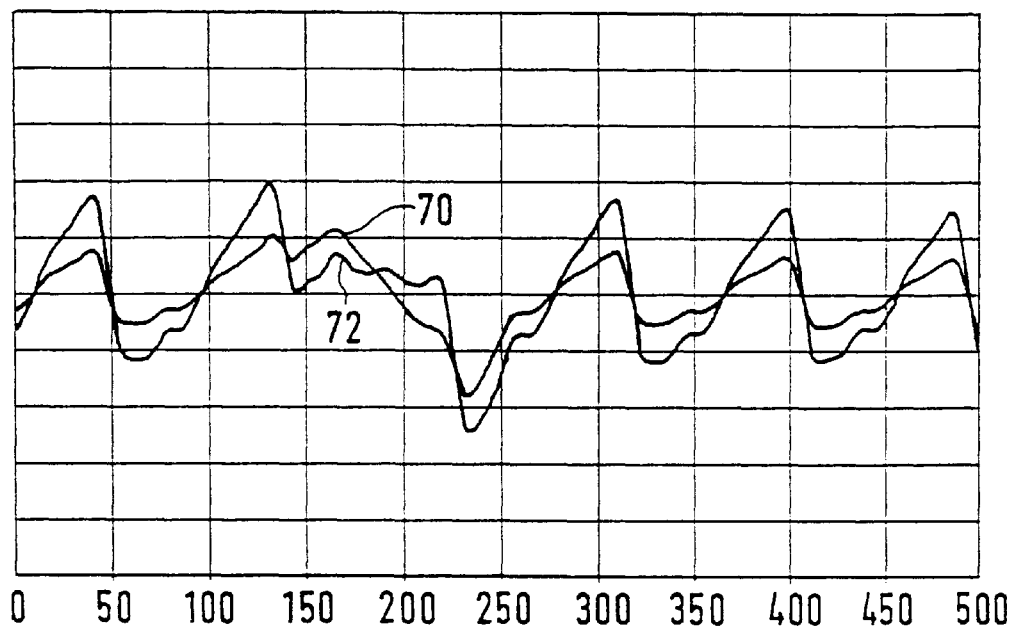
FIG. 7 shows a diagram of disturbed alternating components.

FIG. 5 shows a diagram of the two AC signals AC1[i], curve 50, and AC2[i], curve 52, over a window of 500 samples i. A disturbance a[i] which originates from a motion artifact whose frequency is higher than or equal to the pulse rate and which causes an intensity variation at the photodiode is shown as curve 60 in FIG. 6. In FIG. 7 both disturbed signals AC1s[i], curve 70, and AC2s[i], curve 72, are shown. This figure shows that, during the period in which the disturbance occurs, neither a genuine peak nor a correct zero passage exists for a determination of the pulse duration, especially in cases where the amplitude of the disturbance becomes equal to or larger than the arterial signal amplitude. In these cases, the "classical" known calculation of the saturation according to the "peak-finding" method is not applicable.

The disturbance signal component as such is not known, but only the signals AC1s[i] and AC2s[i] superimposed by this disturbance signal component. It follows that, assuming that the disturbance causes the same phase and deflection for both wavelengths, said disturbance can be eliminated by difference formation:

$$\Delta AC[i]=AC2s[i]-AC1s[i]=AC2[i]-AC1[i] \quad (9)$$

Figure 8:
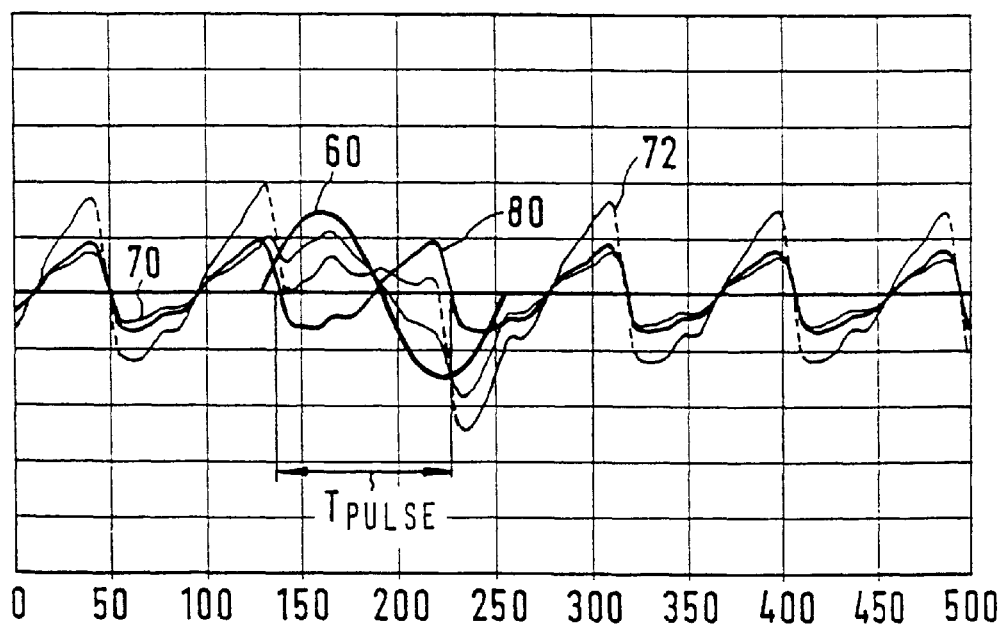
FIG. 8 shows a diagram of a differential value obtained from the disturbed alternating components which are shown in FIG. 7.

The course of this difference curve $\Delta AC[i]$ is shown as curve 80 in FIG. 8. FIG. 8 also shows the correct pulse period Tpulse that can be derived from the respective zero passages of the difference curve. In contrast to known methods, where a pulse rate cannot be determined when such a motion artifact occurs, the method explained hereinbefore permits a determination of the exact pulse rate of the perfusion of human tissue even if such a motion artifact exists.

The prerequisite for the correct artifact elimination is that the DC components for red and infrared are approximately equal. This can be achieved e.g. by means of an unequal LED intensity control. For the case ratio≈1 (equation 13), the $\Delta AC$ difference is zero, but the SpO2 is given to e.g. 85%, even if there are artifacts superimposed. To calculate a correct pulserate for this case, a finite difference can be produced artificially, e.g. by means of different LED intensities.

As has already been mentioned, the method which has been described hereinbefore making reference to the first aspect of the present invention provides good results for low-frequency disturbed signals. In the following, a method will be described, which, making use of the above-explained differential value $\Delta AC[i]$, permits the formation of a ratio: the concentration of a component, in the case of the preferred embodiment the arterial oxygen saturation, can then also be determined in cases in which e.g. a motion artifact exists.

The ratio R[i] can be written in a form that is equivalent to equation 1:

$$R[i]=\ln(1-AC1[i]/L1avg[i])/\ln(1-AC2[i]/L2avg[i]) \quad (10)$$

For a ratio AC/DC<5% (perfusions<10%) the following simplification can be used without causing any noticeable error:

$$R[i]=AC1[i]/L1avg[i])/AC2[i]/L2avg[i] \quad (11)$$

With the substitution $$AC1[i]AC2[i]-\Delta AC[i] \quad (12)$$

the following result is obtained:

$$R[i]=(1-\Delta AC[i]/AC2[i])\cdot L2avg[i]/L1avg[i] \quad (13)$$

Instead of replacing AC1[i], also AC2[i] could be replaced in an equivalent manner in the above equations 8 and 9. Hence, the method explained hereinbelow can also be carried out by means of the alternating component AC1[i] instead of the alternating component AC2[i].

In the case of a disturbance caused by a motion artifact, AC2s[i] would be effective instead of the undisturbed signal AC2[i], $\Delta AC[i]$, however, remains the same for disturbed as well as undisturbed cases, and also the factor L2avg[i]/L1avg[i] remains unchanged under the influence of an artifact.

It follows that, if there is an artifact, the main task will be to recognize this artifact on the one hand and to find the correctest possible (artifact-free) alternating component AC2[i] (or alternatively AC1[i]) on the other.

In the case of a disturbance, it may be advantageous to use for the calculation areas or values integrated over a subperiod instead of using spot curve determination, such as the zero passage or a peak. For this purpose, the respective values can, for example, be integrated over half a period length of the continuous AC difference.

For the continuous AC difference, the following equation is obtained:

$$\Delta AC(T/2) = \sum_{i=1}^{i=T/2} \Delta AC[i] \quad (14)$$

Integrated values for the other quantities AC2[i], L1avg[i], L2avg[i] can be ascertained in a corresponding manner. For these quantities the values AC2[T/2], L1avg[T/2], L2avg[T/2] are obtained. Accordingly, $$R[T/2]=(1-\Delta AC(T/2)/AC2(T/2))\cdot L2avg[T/2]/L1avg[T/2] \quad (15)$$

is obtained for the ratio R for each half pulse period.

Among the quantities underlying the ratio R[T/2], it is essentially only AC2(T/2) that changes due to a disturbance. When the existence of a disturbance is detected, the present invention uses an artifact-free AC2'(T/2) value, which has been determined during a preceding subperiod, for determining a ratio $R'[T/2]$ in accordance with equation (15). This method can be carried out, at least for a specific period, after the recognition of the disturbance and as long as the differential value $\Delta AC(T/2)$ does not change substantially. If no disturbance is detected, the instantaneously detected AC2 value continues to be used to determine the integrated ratio $R[T/2]$.

The existence of an undisturbed value for AC2 can, for example, be assumed as long as: $0.6 \cdot AC2 < AC2s < 1.4 \cdot AC2$. If the value AC2s falls outside this range, this is adjudged to indicate the existence of a disturbance. A disturbance can also be adjudged on the basis of the discrepancy between the zero passages of $\Delta AC[I]$ and $AC2s[i]$, since without a disturbance these zero passages coincide. The value $\Delta AC$ (T/2) as well as the DC ratio L2avg/L1avg respond to a saturation change but not to the artifacts described hereinbefore. It follows that the above-mentioned calculation provides an excellent approximation for detecting the concentration of a component, e.g. an arterial oxygen saturation in a human tissue, by determining the concentration of the component on the basis of the integrated ratio value $R'[T/2]$.

Figure 9:
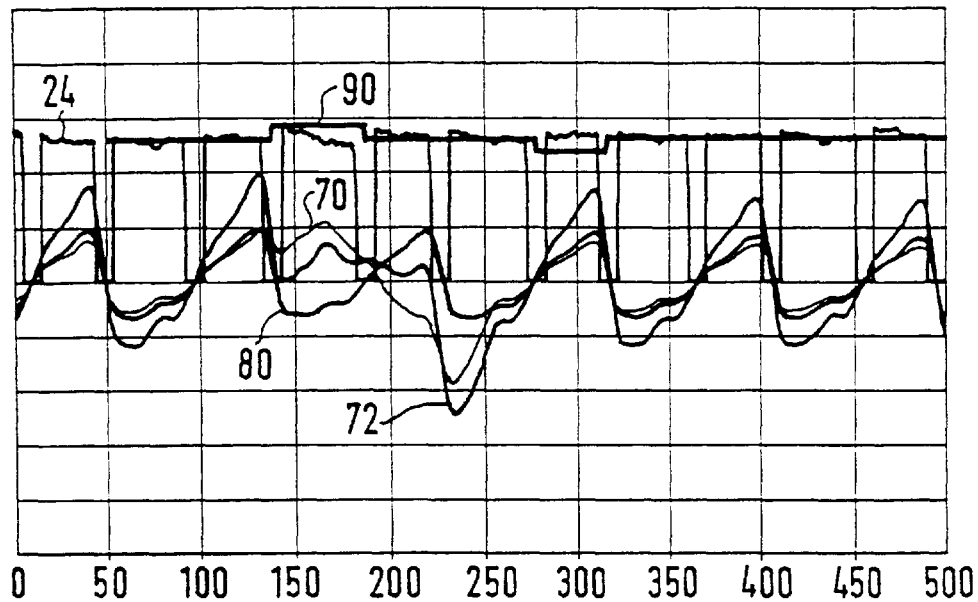
FIG. 9 and 10 show diagrams for illustrating the results obtained by means of the method according to the second aspect of the present invention.

In FIG. 9, the ratio, which has been calculated in accordance with the above approximation method, is shown as curve 90 in comparison with the calculation according to the first aspect on the basis of the undisturbed signals, curve 24.

Figure 10:
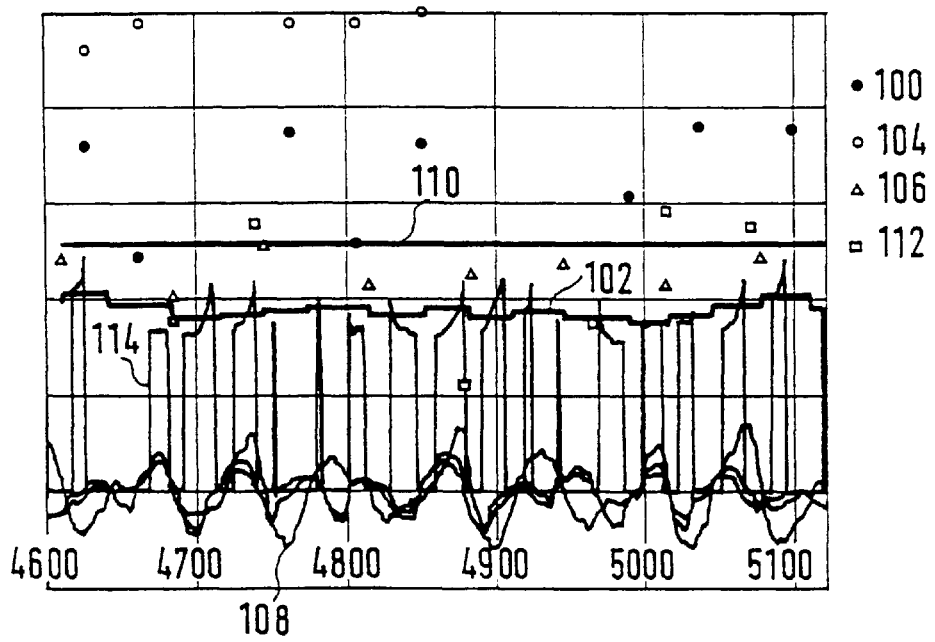

The efficiency of the method described hereinbefore can also be seen from FIG. 10. FIG. 10 shows a detail of an episode with a weak signal, which has been detected by means of an ear sensor, and a strong artifact influence caused e.g. by jogging. The step frequency differs only slightly from the pulse rate.

Conventional peak-finding algorithms trigger here in response to the step frequency, cf. CMS-Sp02 values, dots 100, derived from the algorithm known as "Merlin Sp02 Algorithmus" Rev. 4, and provide a mean saturation value over 512 samples of 84.6%, the standard deviation being ±14.8%. According to the method described hereinbefore with reference to FIG. 4 to 8, a mean saturation value over 512 samples of 94.9% with a standard deviation of ±3.9% is obtained, cf. curve 102; this corresponds to the normal value.

The dots 104 in FIG. 10 represent the averaged pulse rate of 127.4 bmp which has been obtained by means of the above-mentioned conventional method. In accordance with the method according to the present invention, a more precise pulse rate of 113 bpm, cf. dots 106, is obtained.

FIG. 10 additionally shows the two disturbed alternating signals ACs1 [i] and ACs2[i] and the value $\Delta AC \cdot 5$, curve 108, whereas curve 110 represents the continuous DC ratio in FIG. 10. The pulse rate which would be obtained in the case of the method according to the first aspect of the present invention is represented by the dots 112 in FIG. 10.

In the following, a further alternative method for ratio determination in the case of an artifact will be described. The first step is the determination of the continuous ratio R[i] in the manner which has been described hereinbefore with regard to FIG. 1 to 3. Furthermore, the AC difference $\Delta AC[i]$ is formed, and the pulse period that can be derived therefrom, viz from the zero passages thereof. As ratios for determining the oxygen saturation, only those i-samples are then used which, on the one hand, do not pass through the AC zero points and, on the other hand, are formed only with AC2s[i] values having the same direction (SIGN) in the amplitude deflection as the $\Delta AC[i]$ values. This increases the likelihood that more signal components with an undisturbed phase are taken into account, whereas all the oppositely directed are left out of account. This comparatively simple method proved to be useful especially for weak to medium-sized disturbance amplitudes. The signal curve of the resultant saturation averaged over 512 samples, curve 114, which is shown in FIG. 7, refers, however, to a case with strong disturbance amplitude, where AC[i] is approximately equal to a[i]. In this case, a mean saturation value of 90.8% with a standard deviation of ±9.6% was obtained.

I claim:

1. A method of determining the concentration of a component from the intensity of electromagnetic waves with at least two selected wavelengths which are reflected by human tissue or transmitted through human tissue, said method comprising the following steps:

1.1 converting the intensities of received electromagnetic waves into at least one first and one second electric signal;

1.2 forming a continuous first temporal average value of the first signal;

1.3 forming a continuous second temporal average value of the second signal;

1.4 determining a continuous ratio from said first and second signals as well as from said first and second continuous temporal average values with the exception of regions lying close to the zero passages of alternating components of said first signal and said first average value, and said second signal and said second average value; and 1.5 deriving the concentration of the component from said continuous ratio.

2. A method according to claim 1, wherein said derived concentration is the oxygen saturation of a flow of blood.

3. A method according to claim 2, comprising additionally the following step:

3.1 continuously determining a first alternating component from said first signal and said first average value;

3.2 continuously determining a second alternating component from said second signal and said second average value; and 3.3 determining the pulse rate of the flow of blood on the basis of the zero passages of the first or of the second alternating component.

4. A method according to claim 1, wherein the continuous first and second average values are each determined over the duration of a pulse period of said first or second signal.

5. A method according to claim 1, wherein the continuous ratio from which the concentration of the component is derived is determined by the equation $$R(i) = \ln(L1(i)/L1avg(i))/\ln(L2(i)/L2avg(i)),$$

wherein L1(i) is the first signal, L2(i) is the second signal, L1avg(i) is the continuous first temporal average value and L2avg(i) is the continuous second temporal average value.

6. A method according to claim 1, wherein the first alternating component is formed by subtracting the continuous first temporal average value from the first signal and wherein the second alternating component is formed by subtracting the continuous second temporal average value from the second signal.

7. A method of determining the concentration of a component from the intensity of electromagnetic waves with at least two selected wavelengths which are reflected by human tissue or transmitted through human tissue, said method comprising the following steps:

7.1 converting the intensities of received electromagnetic waves into at least one first and one second electric signal;

7.2 forming a continuous first temporal average value of the first signal;

7.3 forming a continuous second temporal average value of the second signal;

7.4 continuously determining a first alternating component from said first signal and said first average value;

7.5 continuously determining a second alternating component from said second signal and said second average value;

7.6 determining a continuous differential value of the two alternating components;

7.7 determining a first integrated average value by integrating the first average value over a subperiod of said continuous differential value;

7.8 determining a second integrated average value by integrating the second average value over said subperiod;

7.9 determining an integrated alternating component by integrating the first or the second alternating component over said subperiod;

7.10 determining a first integrated differential value by integrating said differential value over said subperiod;

7.11 determining an integrated ratio value on the basis of the integrated differential value, the integrated alternating component and the two integrated average values; and 7.12 deriving the concentration of the component from the integrated ratio value.

8. A method according to claim 7, wherein the subperiod used in each of the steps 7.7 to 7.10 is a half period of the continuous differential value.

9. A method according to claim 7, wherein the concentration of the component being determined is an arterial oxygen saturation.

10. The method of claim 7, further comprising:

subsequent to step 7.10, judging the first or second alternating component as disturbance free or as subjected to a disturbance; and if the instantaneous first or second alternating component is judged as disturbance free, executing steps 7.11 and 7.12;

otherwise:

determining an integrated ratio value on the basis of the integrated differential value, the integrated alternating component determined during the preceding subperiod for which the integrated alternating component determined has been judged as disturbance free, and the two integrated average values whose ratio stays constant under artifacts, but not at sudden concentration changes; and executing step 7.12.

11. A method according to claim 10, wherein the first or the second alternating component is judged as disturbance free in step 7.11 when: 0.6·AC<Acs<1.4·AC, wherein AC is a value of the disturbance-free alternating component and ACs is a value of the alternating component which is subjected to a disturbance.

12. A method according to claim 10, wherein in step 7.11 the first or the second alternating component is judged on the basis of the zero passages of the differential value and the first or second alternating component.

13. A method of determining a pulse rate of a flow of blood through human tissue from the intensity of electromagnetic waves with at least two selected wavelengths which are reflected by said human tissue or transmitted through said human tissue, said method comprising the following steps:

13.1 converting the intensities of received electromagnetic waves into at least one first and one second electric signal;

13.2 forming a continuous first temporal average value of the first signal;

13.3 forming a continuous second temporal average value of the second signal;

13.4 continuously determining a first alternating component from said first signal and said first average value;

13.5 continuously determining a second alternating component from said second signal and said second average value;

13.6 determining a continuous differential value of the two alternating components; and 13.7 determining the pulse rate of the flow of blood on the basis of the zero passages of said differential value.

14. An apparatus for determining the concentration of a component from the intensity of electromagnetic waves with at least two selected wavelengths which are reflected by human tissue or transmitted through human tissue, comprising:

means for converting the intensities of received electromagnetic waves into at least one first and one second electric signal;

means for forming a continuous first temporal average value of the first signal;

means for forming a continuous second temporal average value of the second signal;

means for determining a continuous ratio from said first and second signals as well as from said first and second continuous temporal average values with the exception of regions lying close to the zero passages of alternating components of said first signal and said first average value, and said second signal and said second average value; and means for deriving the concentration of the component from said continuous ratio.

15. An apparatus according to claim 13, wherein the concentration of the component being determined is arterial oxygen saturation.

16. An apparatus for determining the concentration of a component from the intensity of electromagnetic waves with at least two selected wavelengths which are reflected by human tissue or transmitted through human tissue, comprising:

means for converting the intensities of received electromagnetic waves into at least one first and one second electric signal;

means for forming a continuous first temporal average value of the first signal;

means for forming a continuous second temporal average value of the second signal;

means for continuously determining a first alternating component from said first signal and said first average value;

means for continuously determining a second alternating component from said second signal and said second average value;

means for determining a continuous differential value of the two alternating components;

means for determining a first integrated average value by integrating the first average value over a subperiod of said continuous differential value;

means for determining a second integrated average value by integrating the second average value over said subperiod;

means for determining an integrated alternating component by integrating the first or the second alternating component over said subperiod;

means for determining a first integrated differential value by integrating said differential value over said subperiod;

means for determining a first integrated ratio value on the basis of the integrated differential value, the integrated alternating component and the two integrated average values; and means for deriving the concentration of the component from the first integrated ratio value.

17. The apparatus of claim 16, further comprising:

means for judging the first or second alternating component as disturbance free or as subjected to a disturbance;

means for deriving the concentration of the component from the first integrated ratio value if the instantaneous first or second alternating component is judged as disturbance free by said means for judging; and means for determining a second integrated ratio value on the basis of the integrated differential value, the integrated alternating component determined during the preceding subperiod for which the integrated alternating component determined has been judged as disturbance free, and the two integrated average values; and means for deriving the concentration of the component from the second integrated ratio value if the instantaneous first or second alternating component is not judged as disturbance free by said means for judging.

18. An apparatus for determining a pulse rate of a flow of blood through human tissue from the intensity of electromagnetic waves with at least two selected wavelengths which are reflected by said human tissue or transmitted through said human tissue, comprising:

means for converting the intensities of received electromagnetic waves into at least one first and one second electric signal;

means for forming a continuous first temporal average value of the first signal;

means for forming a continuous second temporal average value of the second signal;

means for continuously determining a first alternating component from said first signal and said first average value;

means for continuously determining a second alternating component from said second signal and said second average value;

means for determining a continuous differential value of the two alternating components; and means for determining the pulse rate of the flow of blood on the basis of the zero passages of said differential value.

* * * * *